United States Patent [19]

Okayama et al.

[11] 4,368,298

[45] Jan. 11, 1983

[54] PROCESS FOR PRODUCING NOVOLAK-TYPE EPOXY RESIN

[76] Inventors: Kiyoaki Okayama, 66-15, Sasagawa 8-chome, Yokkaichi-shi, Mie-ken; Makoto Nishizuka, 1665, Kubo-cho, Matsusaka-shi, Mie-ken, both of Japan

[21] Appl. No.: 234,548

[22] Filed: Feb. 13, 1981

[30] Foreign Application Priority Data

Feb. 20, 1980 [JP] Japan .................................. 55-18979

[51] Int. Cl.[3] .......................... C08G 8/10; C08G 8/28

[52] U.S. Cl. .................................... 525/480; 525/507; 528/105; 528/154

[58] Field of Search ..................... 528/87, 129, 88, 99, 528/100, 105, 102, 154; 525/480, 507; 260/348.19

[56] References Cited

U.S. PATENT DOCUMENTS

| | | | |
|---|---|---|---|
| 2,390,198 | 12/1945 | Voss et al. | 528/129 |
| 2,892,809 | 6/1959 | St. Clair | 525/480 |
| 3,067,171 | 12/1962 | Hoppe | 260/348.19 |
| 3,867,346 | 2/1975 | Vargin et al. | 528/129 |

*Primary Examiner*—Allan Lieberman

[57] ABSTRACT

A process for producing a novolak-type epoxy resin, which comprises reacting a halohydrin ether of a phenol compound with an aldehyde compound in the presence of an acid catalyst, and thereafter treating the product with a cyclizing agent to form an epoxy ring.

7 Claims, No Drawings

PROCESS FOR PRODUCING NOVOLAK-TYPE EPOXY RESIN

This invention relates to a process for producing a novolak-type epoxy resin, and more specifically, to a process for easily producing a novolak-type epoxy resin which has a reduced content of phenolic hydroxyl groups and good storage stability, and can give cured products having high heat resistance.

According to the prior art, a novolak-type epoxy resin is produced by reacting a phenol compound with an aldehyde compound in the presence of an acid catalyst, and reacting the resulting novolak with an epihalohydrin to introduce an epoxy group. Investigations of the present inventors have shown that in the prior art process, the terminal phenolic hydroxyl groups of the novolak completely react with the epihalohydrin but the sterically hindered phenolic hydroxyl groups of the novolak have low reactivity with the epihalohydrin and are difficult to react completely with the epihalohydrin, and therefore these hydroxyl groups tend to remain free, and this tendency is especially outstanding when it is desired to produce a high-molecular-weight epoxy resin. It is also noted that because an epoxy resin containing many such residual phenolic hydroxyl groups has poor heat stability and its cured product has a low crosslinking density, the cured product has a low heat-resistant temperature.

It is an object of this invention therefore to provide a novolak-type epoxy resin having a reduced content of phenolic hydroxyl groups and good heat stability which can be cured to a product having a high crosslinking density and excellent heat resistance.

It has now been found in accordance with this invention that the aforesaid object can be achieved by reacting a phenol compound with an epihalohydrin to form a halohydrin ether, reacting it with an aldehyde compound to form a novolak, and then treating the novolak with a cyclizing agent to form an epoxy ring.

According to this invention, there is provided a process for producing a novolak-type epoxy resin, which comprises reacting a halohydrin ether of a phenol compound with an aldehyde compound in the presence of an acid catalyst, and then treating the resulting product with a cyclizing agent to form an epoxy ring.

The process of this invention brings about the following excellent advantages.

(1) The content of residual phenolic hydroxyl groups in the resulting resin can be markedly reduced, and a novolak-type epoxy resin can be easily obtained which has good storage stability and can give a cured product having a high heat-resistant temperature.

(2) In the prior art, it is difficult to obtain a solid novolak-type epoxy resin of high quality, and it is only normally semisolid, low-molecular-weight novolak-type epoxy resins that are commercially available. In contrast, according to the process of this invention, a normally solid, high-molecular-weight novolak-type epoxy resin of high quality can be easily produced, and advantageously used in applications which require solid resins, for example in powder molding.

(3) A low-molecular-weight novolak-type epoxy resin can also be produced easily if the mole ratio of the halohydrin ether of the phenol compound to the aldehyde compounds is properly selected. For example, a novolak-epoxy resin consisting substantially of a difunctional epoxy compound can be easily obtained by reacting the halohydrin ether with a relatively small amount of the aldehyde compound, and removing the unreacted halohydrin ether and/or monoepoxide from the resulting reaction product.

In the process of this invention, the starting halohydrin ether of a phenol compound or the reaction product of the ether with an aldehyde compound may of course be subjected, prior to use in a subsequent step, to an additional step for isolating the reaction product, separating the unreacted matter, neutralizing or separating the residual catalyst, for example distillation at atmospheric and/or reduced pressure, washing with a suitable washing solvent, or addition of an acid or alkali.

The phenol compound used to obtain the halohydrin ether is generally expressed by the following formula.

OH — benzene ring — $(R^1)_m$ (I)

wherein $R^1$ represents an alkyl group having 1 to 9 carbon atoms which may be substituted by an amino group or an N-alkylamino group, a hydroxyl group, an amino group, an amido group, a carboxyl group or a halogen atom, and m represents zero or an integer of 1 to 4, provided that when m is two or more, the $R^1$ groups may be identical or different.

Specific examples include phenol; alkyl-substituted phenols such as cresol, tert. butyl phenol, sec. butyl phenol, xylenol, ditert. butyl phenol, ditert. butyl cresol, nonyl phenol and cumyl phenol; polyhydric phenols such as catechol and resorcinol; phenols substituted by nitrogen-containing groups such as 2-dimethylaminomethyl phenol, aniline phenol and acetamidophenol; halophenols such as dibromocresol; and p-hydroxybenzoic acid and α-naphthol. A mixture of two or more of these phenol compounds may be used.

The epihalohydrin used to react with the phenol compound to form the halohydrin ether is represented by the following formula $$\underset{\diagdown\,O\,\diagup}{CH_2\text{—}CH}\text{—}CH_2X \qquad (II)$$

wherein X represents a halogen atom. Usually, epichlorohydrin is used, but epibromohydrin and methylepichlorohydrin can also be used.

The halohydrin ether of a phenol favorably used in this invention is a compound of the following formula

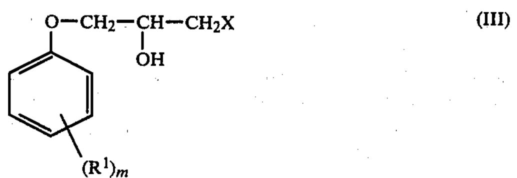

(III)

wherein $R^1$ represents a substituent group or atom, m represents zero or an integer of 1 to 4, provided that when m is 2 or more, the $R_1$ groups may be identical or different, and X represents a halogen atom.

In the process of this invention, two or more of the compounds of general formula (III) may be used in admixture. There can also be used an impure halohydrin ether reaction product containing at least 50% by weight in total of the compound of general formula (III).

The epihalohydrin ether may also contain a by-product of the formula

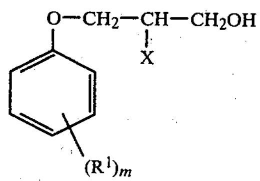

wherein $R^1$, X and m are as defined above.

The aldehyde compound to be reacted with the halohydrin ether of formula (III) may be any known aldehyde compounds used in the production of phenol-aldehyde resins, and compounds which on decomposition yield these aldehyde compounds can also be used.

These aldehyde compounds can be represented by the following general formula $$R^2\text{—CHO} \qquad (IV)$$

wherein $R^2$ represents a hydrogen atom, an aliphatic group, an aromatic group or a heterocyclic group.

Examples include aliphatic aldehydes such as formaldehyde, acetaldehyde and propionaldehyde; aromatic aldehydes typified by benzaldehyde; and heterocyclic aldehydes typified by furfural. Hexamethylene tetramine, paraaldehyde and paraformaldehyde are examples of the aldehyde compounds which on decomposition yield the above aldehyde compound. If desired, a mixture of two or more of these aldehyde compounds may be used.

The chemical reactions involved in the process of this invention including the reaction of forming the halohydrin ether of a phenol compound are schematically shown below with reference to the case of using phenol as the phenol compound, formaldehyde as the aldehyde compound and epichlorhydrin as the epihalohydrin.

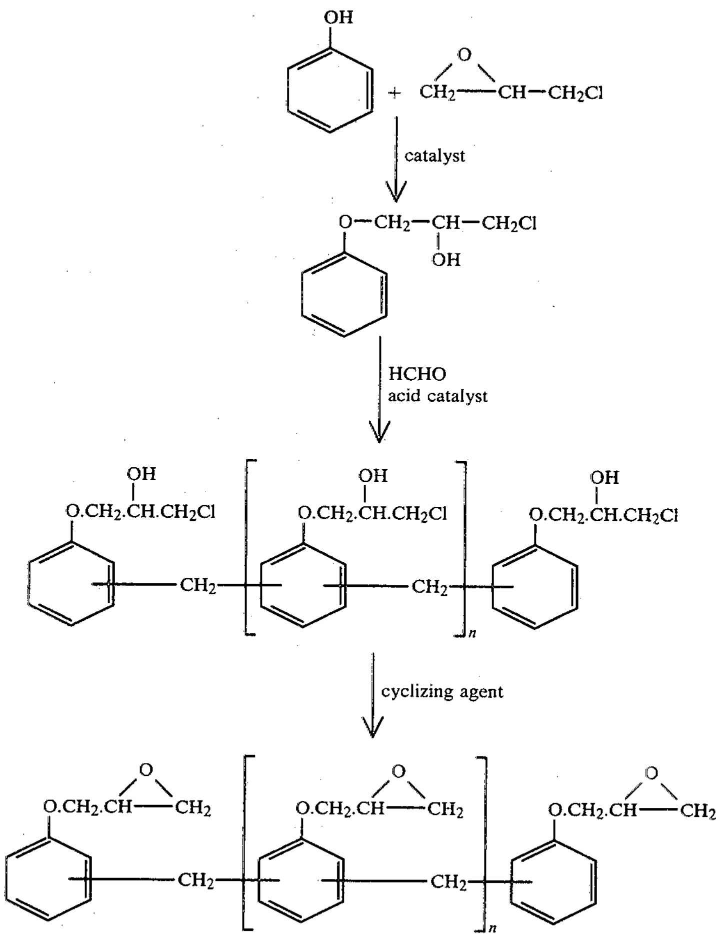

In the reaction of forming the halohydrin ether of the phenol compound used in this invention, the mole ratio of epihalohydrin to the phenol compound used in the reaction is usually from 1 to 5, preferably from 1.5 to 3.

In this reaction, an initial-stage catalyst and a later-stage catalyst are usually employed, but the latter is not essential.

Quaternary ammonium salts such as tetramethyl ammonium chloride, tetraethyl ammonium chloride and tetramethyl ammonium bromide, and tertiary amines such as triethylamine and N,N'-dimethylaniline are used as the initial-stage catalyst. Such quaternary ammonium salts as tetramethyl ammonium chloride and tetramethyl ammonium bromide are preferred because of their high catalytic activity and low cost. The amount of the initial-stage catalyst is such that the mole ratio of the catalyst to the phenol compound is usually from 0.001 to 0.05, preferably from 0.005 to 0.02.

As the later-stage catalyst, an alkali metal hydroxide such as sodium hydroxide and potassium hydroxide, and an alkali metal hydride such as lithium hydride are normally used. The mole ratio of the latter-stage catalyst to the phenol compound is usually from 0 to 0.5, preferably from 0.1 to 0.3.

In a typical example of reacting the phenol compound with the epihalohydrin, the phenol compound, epihalohydrin and initial-stage catalyst are charged, and reacted at 70° to 140° C., preferably 80° to 120° C., for 30 minutes to 5 hours, preferably 30 minutes to 3 hours, and as required, the reaction is subsequently performed at the same temperature for 30 minutes to 3 hours, preferably 1 to 2 hours, while adding dropwise the later-stage catalyst (e.g., a 50% aqueous solution of NaOH). Then, while removing the epihalohydrin, the temperature is raised to 140° C. at the highest, and the pressure is gradually reduced. The temperature is adjusted to 120° C. or below, and under a reduced pressure of, for example, 10 mmHg, the excess of epihalohydrin is removed as an azeotrope with water. Preferably, hydrochloric acid (e.g., 10–38% aqueous HCl solution) is added dropwise at a temperature of 60° to 100° C. over a period of 1 to 2 hours in an amount of 1.0 to 1.2 moles per mole of the alkali metal hydroxide as the later-stage catalyst to cyclize completely the epoxy group of the resulting compound. Then, the product is washed with water, and water is removed at a temperature of not more than 140° C. and a reduced pressure of, for example, 10 mmHg. At the time of washing with water, the wash water forms an upper layer because of the high specific gravity of the resulting product. Hence, a suitable solvent such as toluene or methyl isobutyl ketone is added to reverse the compound layer and the aqueous layer, thus facilitating separation of the aqueous layer. The solvent is removed in the same way as in the removal of the epihalohydrin.

The mole ratio of the aldehyde compound to the halohydrin ether of the phenol compound (to be referred to simply as the "halohydrin ether") in this invention is properly selected from the range of 0.1 to 3 depending upon the properties, uses, etc. of the desired epoxy resin. In this reaction, an acid catalyst such as sulfuric acid, hydrochloric acid, phosphoric acid and perchloric acid is used. A Lewis acid such as $BF_3$ and $SnCl_4$, a solid acid catalyst such as $SiO_2$. $Al_2O_3$ and $SiO_2.TiO_2$, and a strong acid such as $H_2SO_4$—$SO_3$ and $HSO_3F$ may also be used. The equivalent ratio of the acid catalyst to the halohydrin ether is usually from 0.01 to 1.0, preferably from 0.1 to 0.5.

In a typical embodiment of performing this reaction, the halohydrin ether and the acid catalyst are heated to 70° to 110° C., and the aldehyde compound is added dropwise over a period of usually 30 minutes to 5 hours, preferably 1 to 3 hours. The reaction time may further be extended, if required. This reaction can be carried out in various modified embodiments. For example, when it is desired to produce a high-molecular-weight resin, an aldehyde compound such as formaldehyde and acetaldehyde may be added dropwise to the acid catalyst to polymerize the aldehyde compound to paraldehyde or paraformaldehyde, and the halohydrin ether may be added and reacted with it. Alternatively, a polymer such as paraldehyde or paraformaldehyde is used as the aldehyde compound, and while heating it to perform depolymerization the halohydrin ether may be added to induce dehydrocondensation reaction. In another embodiment, the reaction between the halohydrin ether and the aldehyde may be carried out while removing water by reducing the pressure of the reaction system.

Desirably, the product obtained by this reaction is purified, prior to use in the epoxy ring-forming reaction, by dissolving it in a suitable solvent such as methyl isobutyl ketone, toluene or xylene, and separating the acid catalyst and/or washing the solution to remove it.

The epoxy ring-forming reaction in the process of this invention is carried out by heating the purified reaction product between the halohydrin ether and the aldehyde compound (to be sometimes referred to as the "halohydrin etherified novolak") to a temperature of, usually, 70° to 120° C., preferably 80° to 100° C., and adding a suitable cyclizing agent, for example a 50% aqueous solution of sodium hydroxide, dropwise to it, thereby forming an epoxy ring by cyclization accompanied by dehydrochlorination.

Sodium hydroxide and potassium hydroxide are the preferred examples of the cyclizing agent. The suitable amount of the cyclizing agent is from 0.9 to 1.5 moles, preferably from 0.95 to 1.1 moles, per mole of the halogen in the halohydrin etherified novolak.

The resin obtained after the above reaction is washed with water, and the solvent is removed by heating under reduced pressure. The resulting product can be used as a novolak-type epoxy resin.

The following Examples illustrate the present invention more specifically.

EXAMPLE 1

First step

A one-liter four-necked glass flask equipped with a stirrer, a dropwise addition device, a reflux device and a thermometer was charged with 188 g (2 moles) of phenol, 370 g (4 moles) of epichlorohydrin and 3.08 g (0.02 mole) of tetramethyl ammonium bromide, and they were reacted at 100° to 120° C. for 30 minutes. Then, 33 g (0.4 mole as NaOH) of a 48.5% by weight aqueous solution of sodium hydroxide was added dropwise at 90° to 100° C. for 30 minutes. The reaction was continued at this temperature for 30 minutes, and the reaction mixture was heated to a temperature of 120° C. at the highest while reducing the pressure gradually from atmospheric pressure to 10 mmHg, thereby removing water and the unreacted epichlorohydrin. The product was cooled to 100° C., and 44.6 g (0.44 mole as HCl) was added dropwise at 90° to 100° C. over 60 minutes. The mixture was stirred at this temperature for 30 minutes. Then, it was washed repeatedly with water until the pH of the wash water reached at least 6. The product was then heated to a temperature of 120° C. at the highest under a pressure of 10 mmHg to remove water. There was obtained 362 g of a colorless clear liquid.

The product had a specific gravity of 1.2212, a viscosity of 81 centipoises at 25° C., a hydrolyzable chlorine content of 18.7% by weight (19.0% by weight as calculated), an epoxy group content of less than 0.01 milliequivalent/g and a phenolic hydroxyl group content of less than 0.01 milliequivalent/g.

The high-speed chromatographic chart of this product corresponded with that of a separately obtained HCl adduct of phenyl glycidyl ether (i.e., glycylomonochlorohydrin phenyl ether).

Second step

A 0.5 liter glass flask provided with the same attachments as in the flask used in the first step was charged with 93.3 g of glycylomonochlorohydrin phenyl ether obtained in the first step and 17.5 g of 70% sulfuric acid, and while maintaining the reaction temperature at 70° to 100° C., 34.3 g of 35% formalin was added dropwise over 2 hours. The reaction was continued at this temperature for 2 hours.

The resulting resin was dissolved in 150 ml of methyl isobutyl ketone, and repeatedly washed with water until the pH of the wash water reached at least 6.

The product had a hydrolyzable chlorine content of 17.9% by weight.

Third step

To the purified resin obtained in the second step, 41 g of a 48.5% by weight aqueous solution of sodium hydroxide was added dropwise at 80° C. over 2 hours, and the reaction was continued at 80° to 90° C. for 30 minutes. Then, the product was repeatedly washed with water until the pH of the wash water reached 8 or below, and then the methyl isobutyl ketone solvent was removed by heating the product at 130° C. under a reduced pressure of 10 mmHg. The amount of the resin obtained was 76.0 g.

The resin so obtained was a reddish brown solid and had an epoxy equivalent of 187 g/equivalent, a hydrolyzable chlorine content of 0.10% by weight, a phenolic hydroxyl group concentration of less than 0.01 milliequivalent/g, and a softening point, determined by the Duranes' method, of 53° C.

EXAMPLE 2

First step

Glycylomonochlorohydrin phenyl ether was prepared in the same way as in the first step of Example 1.

Second step

Conc. sulfuric acid (19 g) was put into the same flask as used in the second step of Example 1, and while cooling it with a water bath, 55 g of formalin (35% by weight) was added dropwise. Then, 120 g of the glycylomonochlorohydrin phenyl ether produced in the first step was added, and reacted at 100° to 110° C. for 5 hours. The product was dissolved in 250 ml of methyl isobutyl ketone, and washed with water in the same way as in the second step of Example 1.

Third step

The product obtained in the second step was subjected to cyclization reaction in accordance with the procedure of the third step of Example 1. The reaction product was washed with water and the solvent was removed. The amount of 48.5% by weight sodium hydroxide was 55.7 g.

The resulting resin was a reddish brown solid having a softening point, determined by the Duranes' method, of 74° C., an epoxy equivalent of 196 g/equivalent, a hydrolyzable chlorine content of 0.15 equivalent, a phenolic hydroxyl group concentration of less than 0.01 milliequivalent/g, and a solution viscosity, determined by the Gardner-Holtz method for a 40% by weight butyl carbitol solution at 25° C., of E to F. The yield of the resin was 99 g.

EXAMPLE 3

First step

The same reaction and purification as in the first step of Example 1 were carried out except that 200 g of o-cresol, 513.5 g of epichlorohydrin, 2.85 g of tetramethyl ammonium bromide, 61 g of a 48.5% by weight aqueous solution of sodium hydroxide and 85 g of conc. hydrochloric acid (35% by weight). The amount of the product was 352 g.

The product (glycylomonochlorohydrin o-cresyl ether) was a pale yellow liquid having a specific gravity of 1.197, a viscosity of 75 centipoises at 25° C., a hydrolyzable chlorine content of 17.3% by weight (17.7% by weight as calculated), an epoxy group content of less than 0.01 milliequivalent/g and a phenolic hydroxyl group content of less than 0.01 milliequivalent/g.

Second and third steps

The same reaction and purification were performed in the same way as in the second and third steps of Example 1 except that 140 g of the product obtained in the first step above, 54 g of formalin (35% by weight), 21 g of 70% sulfuric acid, 250 ml of methyl isobutyl ketone, and 58 g of a 48.5% by weight aqueous solution of sodium hydroxide were used. There was obtained 116 g of a reddish brown solid resin.

The resulting resin had an epoxy equivalent of 210 g/equivalent, a hydrolyzable chlorine content of 0.16% by weight, a phenolic hydroxyl group concentration of less than 0.01 milliequivalent/g, and a softening point, determined by the Duranes' method, of 61° C.

EXAMPLE 4

First step

Glycylomonochlorohydrin phenyl ether was prepared in the same way as in the first step of Example 1.

Second and third steps

The same reaction and purification as in the second and third steps of Example 1 were performed except that 186.5 g of the glycylomonochlorohydrin phenyl ether obtained in the first step, 30 g of 70% sulfuric acid, 26 g of formalin (35% by weight), 83 g of a 48.5% by weight aqueous solution of sodium hydroxide and 300 ml of toluene as a solvent were used. There was obtained 148 g of a pale yellow liquid resin.

The resulting resin had a viscosity of 18 poises at 25° C., an epoxy equivalent of 166 g/equivalent, a hydrolyzable chlorine content of 0.09% by weight, and a phenolic hydroxyl group concentration of less than 0.01 milliequivalent/g.

Experimental Example

The epoxy resins obtained in Examples 1 to 4 and commercially available Epikote 154 (a trademark) were each cured, and the heat distortion temperatures of the cured products were measured. The results are tabulated below.

| Epoxy resin | Heat distortion temperature (°C.) |
|---|---|
| Resin of Example 1 | 172 |
| Resin of Example 2 | 195 |
| Epikote 154 | 180 |
| Resin of Example 3 | 280 |

-continued

| Epoxy resin | Heat distortion temperature (°C.) |
|---|---|
| Resin of Example 4 | 113 |

Note 1

Epikote 154 was obtained by a conventional manufacturing method from the same types and amounts of materials as in Example 2.

Note 2

The heat distortion temperature was measured by the following method.

Recipe: Epoxy resin/curing agent/curing accelerator=100/100/1.5 (by weight)

Curing conditions: 90° C./2 hours+200° C./16 hours

Curing agent: "Nadic Methyl Anhydride" (Kayahard CD, a trademark for Nippon Kayaku Co., Ltd.)

Others: Other conditions are in accordance with ASTM-D-648.

It is seen from a comparison of the resin in Example 2 with Epikote 154 that despite the fact that the types and proportions of the starting materials are the same, the resin of Example 2 has a markedly higher heat distortion temperature than Epikote 154 produced by the conventional method, and has better heat resistance.

EXAMPLE 5

First step

The same reaction and purification as in the first step of Example 1 were carried out except that 133 g of dibromocresol, 139 g of epichlorohydrin and 0.8 g of tetramethyl ammonium hydroxide, 16.5 g of a 48.5% by weight aqueous solution of sodium hydroxide and 25 g of conc. hydrochloric acid (35% by weight) were used. The amount of the product was 165 g.

Second and third steps

The same reaction and purification as in the second and third steps of Example 1 were carried out except that 108 g of the product obtained in the first step, 24.4 g of formalin (35% by weight), 9 g of 70% sulfuric acid, 280 ml of methyl isobutyl ketone, and 26 g of a 48.5% by weight aqueous solution of sodium hydroxide were used. There was obtained 89 g of a reddish brown solid resin.

The resin had an epoxy equivalent of 425 g/equivalent and a hydrolyzable chlorine content of 0.25% by weight.

EXAMPLE 6

First step

The same reactor as used in the first step of Example 1 was charged with a solution of 43.6 g of p-aminophenol, 370 g of epichlorohydrin and 0.58 g of lithium hydroxide hydrate in 25 ml of pure water, and addition reaction was carried out at 35° C. for 25 hours. The temperature was further raised to 40° C., and 40 g of a 48.5% by weight aqueous solution of sodium hydroxide was added dropwise over 3 hours, followed by heating at 40° C. for 2 hours. While reducing the pressure gradually from atmospheric pressure to 2 mmHg, the mixture was heated to a temperature of 70° C. at the highest to remove water and the unreacted epichlorohydrin.

Then, while maintaining the temperature at 70° C., 53 g of conc. hydrochloric acid (35% by weight) was added dropwise over 60 minutes, and the mixture was stirred for 30 minutes at this temperature. The product was washed with water until the pH of the wash water reached at least 6. Water was removed by heating the washed product under reduced pressure of 5 mmHg to a temperature of 70° C. at the highest. There was obtained 142 g of a yellowish brown clear liquid having a hydrolyzable chlorine content of 26.5% by weight (27.6% by weight as calculated).

Second step

The same reaction and purification as in the second step of Example 1 were performed except that 116 g of the product obtained in the first step, 24.4 g of formalin (35% by weight), 9 g of 70% sulfuric acid and 300 ml of methyl isobutyl ketone were used.

Third step

To the purified resin obtained in the second step was added dropwise 74 g of a 48.5% by weight aqueous solution of sodium hydroxide at 40° C. over 3 hours, and the reaction was continued at 40° C. for 3 hours. The product was washed with water until the pH of the wash water reached 8 or below, and the methyl isobutyl ketone was removed at 70° C. and 5 mmHg. The amount of the resin was 81 g.

What we claim is:

1. A process for producing a novolak-type epoxy resin, which comprises:

reacting (a) a halohydrin ether of a phenol compound of the formula

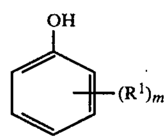

wherein $R^1$ represents alkyl having 1 to 9 carbon atoms which may be substituted by amino or N-alkylamino; hydroxyl; amino; amido; carboxyl; or halogen, and m represents zero or an integer of 1 to 4, provided that when m is 2 or more, the $R^1$ groups may be identical or different, with (b) an aldehyde compound, in the presence of an acid catalyst, the mole ratio of the aldehyde compound to the halohydrin ether being within the range of from 0.1 to 3, the equivalent ratio of the acid catalyst to the halohydrin ether being within the range of from 0.01 to 1.0, and treating the resultant halohydrin etherified novolak with at least one cyclizing agent selected from the group consisting of sodium hydroxide and potassium hydroxide, the amount of the cyclizing agent being within the range of from 0.9 to 1.5 moles per mole of hydrogen in the halohydrin etherified novolak, to form an epoxy ring.

2. The process of claim 1 wherein the halohydrin ether of the phenol compound is a compound of the formula

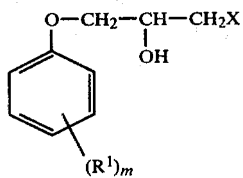

wherein $R^1$ and m are as defined in claim 1, and X represents halogen, or a mixture of compounds represented by said formula.

3. The process of claim 1 wherein the halohydrin ether of the phenol compound is the reaction product obtained by reacting a phenol compound of the formula

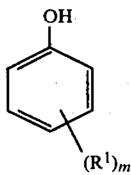

wherein $R^1$ and m are as defined in claim 1, with an epihalohydrin of the formula

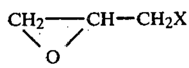

wherein X represents halogen, said reaction product containing at least 50% by weight of the halohydrin ether of the phenol compound of the formula

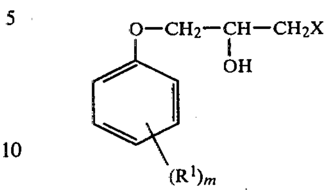

wherein $R^1$, m and X are as defined above.

4. The process of claim 1 wherein the aldehyde compound is a compound of the formula $$R^2\text{—CHO}$$

wherein $R^2$ represents a hydrogen atom, an aliphatic group, an aromatic group or a heterocyclic group, a compound capable of yielding said compound upon decomposition, or a mixture of at least two of these compounds.

5. The process of claim 1 wherein the reaction between the halohydrin ether and the aldehyde is carried out at a temperature of 70° to 110° C.

6. The process of claim 1 wherein the acid catalyst is selected from the group consisting of sulfuric acid, hydrochloric acid, phosphoric acid, perchloric acid, $BF_3$, $SnCl_4$, $SiO_2.Al_2O_3$, $SiO_2.TiO_2$, $H_2SO_4$—$SO_3$ and $HSO_3F$.

7. The process of claim 1 wherein the cyclization reaction to form the epoxy ring is carried out at 70° to 120° C.

* * * * *

UNITED STATES PATENT AND TRADEMARK OFFICE
CERTIFICATE OF CORRECTION

PATENT NO. : 4,368,298
DATED : January 11, 1983
INVENTOR(S) : Kiyoaki OKAYAMA and Makoto NISHIZUKA It is certified that error appears in the above—identified patent and that said Letters Patent is hereby corrected as shown below:

On the title page add --[73] Assignee: YUKA SHELL EPOXY KABUSHIKI KAISHA, Tokyo, Japan--.

Signed and Sealed this

*Twenty-seventh* Day of *December 1983*

[SEAL]

*Attest:*

GERALD J. MOSSINGHOFF

*Attesting Officer* *Commissioner of Patents and Trademarks*